United States Patent [19]
Tu et al.

[11] Patent Number: 6,033,402
[45] Date of Patent: Mar. 7, 2000

[54] ABLATION DEVICE FOR LEAD EXTRACTION AND METHODS THEREOF

[75] Inventors: Hosheng Tu; Cary Hata, both of Tustin, Calif.

[73] Assignee: Irvine Biomedical, Inc., Irvine, Calif.

[21] Appl. No.: 09/161,890

[22] Filed: Sep. 28, 1998

[51] Int. Cl.[7] .................................................. A61B 18/18
[52] U.S. Cl. ............................. 606/41; 607/108; 606/45
[58] Field of Search ............................... 606/41, 45, 48, 606/108; 607/122

[56] References Cited

U.S. PATENT DOCUMENTS

| | | | |
|---|---|---|---|
| 5,423,806 | 6/1995 | Dale et al. | 606/15 |
| 5,620,451 | 4/1997 | Rosborough | 606/108 |
| 5,674,217 | 10/1997 | Wahlstrom et al. | 606/15 |
| 5,697,936 | 12/1997 | Shipko et al. | 606/108 |
| 5,779,715 | 7/1998 | Tu | 606/108 |
| 5,980,515 | 11/1999 | Tu | 606/41 |

*Primary Examiner*—Michael Peffley

[57] ABSTRACT

An improved lead extraction system using a retractable inner catheter having an electrode means comprising memory-shaped Nitinol sheet members and a RF current generator to raise the temperature to above the transitional shape-change temperature of the Nitinol with a sharp cutting edge. The lead extraction system is useful for the extraction and the removal of unwanted lead by a minimal invasive procedure. In another embodiment, fluid infusion and irrigation means at its distal tip section and an electrode means for loosening the target scar tissue by applying radiofrequency energy and cooled fluid to the said electrode and its contacted tissue.

20 Claims, 7 Drawing Sheets

ABLATION DEVICE FOR LEAD EXTRACTION AND METHODS THEREOF

CROSS-REFERENCE TO RELATED APPLICATION

This application is related to application Ser. No. 08/880,837, filed Jun. 23, 1997, now U.S. Pat. No. 5,782,900, granted Jul. 21, 1998.

FIELD OF THE INVENTION

The present invention generally relates to the improved system for cardiac lead extraction. More particularly, this invention relates to an ablation catheter system and methods thereof for clearing the lead passageway and removing an implanted endocardial pacemaker lead and/or an implanted transvenous defibrillation lead from the cardiovascular system of a patient using a memory-shaped electrode means and RF energy.

BACKGROUND OF THE INVENTION

Symptoms of abnormal heart rhythms are generally referred to as cardiac arrhythmias. Various factors affect the human heart rate and contribute to changes of the heart rate from what is termed the normal sinus rate range. These rates generally range in adults from 60 to 100 beats per minute. The heart includes a number of normal pathways, which are responsible for the propagation of electrical signals from an upper chamber to a lower chamber, which are necessary for performing normal systole and diastole functions.

Treatment of arrhythmias may be accomplished by a variety of approaches, including drugs, surgery, implantable pacemakers/defibrillators, and catheter ablation. While drugs may be the treatment of choice for many patients, they only mask the symptoms and do not cure the underlying causes. Surgical and catheter-based treatments can only cure some simple cases. Implantable devices, which are widely used, will correct the arrhythmia and prevent it from occurring unexpectedly.

Cardiac pacemakers, chronically implanted within a patient's body, and connected to a heart by at least one lead, are frequently used to control bradycardiac conditions. Recently, implantable cardioverter-defibrillators, which are also implanted chronically in a patient's body and connected to the heart by at least one lead, can be used to control tachyarrhythmias and life-threatening fibrillations. There are generally two different types of body implantable leads used with cardiac pacemakers: one type, which requires surgery to expose the myocardial tissue, whereby an electrode is affixed to the epicardial tissue; the second type, which can be inserted through a body vessel, such as a vein, into the heart wherein an electrode contacts the endocardiac tissue. In the second type, the endocardial lead is often secured to the heart through the endocardial lining by a helix, hook, or tines affixed to the distal end of the lead. When the end of a lead contacts the lining of the heart at a desired location, the lead may be secured in place by utilizing lead securing means, such as screwing the helix into the heart tissue, anchoring the hook or engaging the tines.

Similarly, cardioverter defibrillators have used both epicardial leads, that is, leads with electrodes attached to the outside of the heart, and endocardial leads, that is, leads inserted into the heart through a body vessel.

With either pacing or defibrillation endocardial leads, fibrotic tissue may eventually encapsulate the leads, especially in areas where there is low velocity blood flow. When small diameter veins, through which the lead passes, become occluded with fibrotic tissue, the separation of the lead from the vein is difficult and can cause severe damage or destruction to the vein. Furthermore, separation may not be possible without constricting the movement of the lead.

In most cases, an endocardial lead will outlast its associated implanted device. However, the lead may become inoperative, or another type of lead may be required. Frequently, the existing lead is left in place, and an additional lead is implanted, rather than risking the removal of the old lead, which was now bonded to the surrounding tissue. Leaving the implanted lead in place, however, particularly in the heart, may further restrict the operation of various heart valves through which the lead passes. If several leads are left in place, operative procedures of the heart and its efficiency may be impaired. In addition, infection may occasionally develop in or around a lead, requiring surgical removal. In some cases, surgical removal may involve open-heart surgery with its accompanying complications, risks, and costs. These risks are significant for the endocardial pacemaker lead. Because the endocardial defibrillation lead is larger and more complex, the complications associated with the removal of a defibrillation lead can be even greater.

Extraction of chronically implanted leads has been difficult in the past. The problems may include lead fragility and scar tissue encountered along the vein, as well as within the heart. Intravascular countertraction techniques using locking stylets and sheaths via the implant vein, or sheaths, snares, and retrieval baskets via the femoral vein have been described in the literature. Among them, scar tissue was the primary reason for partial or failed removal of a lead. Scar tissue was usually present in multiple locations; the venous entry/subclavian area and the ventricle were the most frequent sites.

Several methods for the removal of pacemaker leads have heretofore been proposed. One method involves a lead removal tool that utilizes a hollow, rigid tube and beveled rod tip for engaging and deforming the coil structure of the heart lead. However, if such a lead can not be removed because of some complication, the tip of the tool is nevertheless locked in place and could not be removed from the lead. Consequently, both the tool and the lead would have to be surgically removed. Moreover, the rigid tube of the tool could easily puncture a blood vessel or a heart cavity wall.

Another method for transvenously extracting a lead involves manual manipulation without the use of an external tool. However, such a method is not possible if the lead has become encapsulated in a blood vessel. Moreover, this method puts excessive strain and tension on the polyurethane or silicone insulation surrounding most pacemaker leads. Should the lead break, the broken inner coil and insulation could damage the heart or surrounding blood vessels. Surgical removal of the broken lead would be imperative. Moreover, if the pacemaker lead included tines, a corkscrew, or another fixation device at the tip, pulling on the lead could seriously damage the wall of the heart.

Another technique has been disclosed in U.S. Pat. No. 4,943,289. This method generally includes the use of a stiffening stylet, which can be inserted into the lead, and then engages the inner coil of the lead near the tip, allowing tension to be applied through the stiffening stylet close to the tip of the lead. This technique also uses a pair of telescopic flexible tubes that are positioned over the lead to free fibrotic connections until the tubes are close to the distal tip of the lead. In a related U.S. Pat. No. 5,632,749, Goode et al.

teaches the use of an anchoring project or expandable means associated with the apparatus for lead extraction.

Another method has been disclosed in U.S. Pat. No. 5,620,451. In this patent, Rosborough teaches the use of a flexible coil of flattened ribbon, whereby a cutting surface is provided at the distal end of the coil. It is also disclosed that the coil is radiopaque so that its use may be observed in the body by fluoroscopy or other suitable means.

What is particular interest to the present invention are radiofrequency (RF) ablation protocols, which have been proven to be highly effective in tissue ablation, while exposing a patient to minimal side effects and risks. Radiofrequency energy may be used in cutting the tissue, or separating implant parts and other substrates. Radiofrequency energy may also be utilized to trigger a memory-shaped Nitinol electrode to effect the tissue separating of the scar tissues from the implanted lead. Through a combination of the mechanical rotating cut force of the memory-shaped Nitinol electrode and the radiofrequency energy on a catheter-based device, extraction and removal of an implanted lead becomes feasible and less difficult.

There is therefore a clinical need for a device which comprises a catheter system having a sharp cutting edge of the memory-shaped Nitinol electrode with RF energy delivery capability, that is useful for extraction and removal of undesired lead by minimally invasive procedures.

SUMMARY OF THE INVENTION

In general, it is an object of the present invention to provide an improved catheter system for lead removal of the heart pacemaker leads or cardioverter-defibrillator endocardial leads. It is another object of the present invention to provide a lead extraction system with an electrode means, which is activatable and can be used in ablating an undesired tissue mass, such as a scar tissue or a fibrotic attachment at the venous entry or subclavian area and the ventricle surrounding an implanted lead in a minimally invasive manner. The "activatable electrode means" in this invention includes a memory-shaped Nitinol electrode means having a plurality of sheet members, each sheet member comprising a sharp-edge distal end and can change shape at or above a transitional temperature. Another object of the present invention is to provide a lead extraction system to irrigate the scar tissue site during or after the lead extraction. It is another object of the invention to provide a radiofrequency current to the electrode means for lead separation and extraction. It is still another object of the present invention to provide a temperature sensing means for the electrode means and a temperature controller to sense a temperature measured from the temperature sensing means to control the delivery of the radiofrequency current.

Briefly, heat is generated by supplying a suitable energy source to a device, which is comprised of an electrode means, in contact with the body tissues. A suitable energy source may consist of radiofrequency energy, microwave energy, ultrasonic energy, alternating current energy, or laser energy. The energy can be supplied to the electrode means and subsequently to the tissues through the electrode means. A DIP (dispersive indifferent pad) type pad or electrode that contacts a patient, is connected to the Indifferent Electrode Connector on the RF generator. Therefore, the RF current delivery becomes effective when a close circuit from a RF generator through a patient and returning to the RF generator is formed. When using an alternating current outlet, the generator should be grounded to avoid electrical interference. Heat is controlled by the power of the RF current delivered and by the delivery duration. The standard RF current generator means and its applications through the electrode means to a patient are well known for those who are skilled in the art.

In one embodiment, a lead extraction system comprises a guiding shaft and a retractable inner catheter. The guiding shaft is semi-flexible, strong and non-conductive, so that the lead extraction system can follow the implanted lead to its distal end portion where a scar tissue is attached to the lead, and extract said lead out of a patient. The guiding shaft comprises a shaft distal end, a shaft proximal end, and a plurality of lumens extending therebetween. A handle is secured to the shaft proximal end of the guiding shaft, wherein the handle has a cavity. The retractable inner catheter has an electrode means, a distal tip section, a distal end, a proximal end, and optionally one lumen extending therebetween.

The electrode means has a plurality of memory-shaped Nitinol sheet members that are secured to the distal end of the retractable inner catheter. Each sheet member of the electrode means has a proximal end and a sharp-edge distal end, wherein the proximal ends of the plurality of sheet members are joined at the distal end of the retractable inner catheter. An electrical conductor is attached to the electrode means. A deployment controller is mounted on the handle and secured to the proximal end of the retractable inner catheter. The deployment controller has a deployed state for the retractable inner catheter to deploy outside of the shaft distal end of the guiding shaft. The deployment controller has also a non-deployed state for the retractable inner catheter to be retracted within the electrode lumen of the guiding shaft. This non-deployed state is maintained during the insertion operation of the lead extraction system into a patient, and during withdrawal of the system from said patient. The guiding shaft can be advanced along the existing lead to the scar tissue site to dislodge the lead from said scar tissue by an advancing mechanism at the handle.

In one embodiment, the degree of deployment is controlled by the pushing action of the deployment controller on the handle and is proportional to the pushing distance that is quantifiable. The deployed electrode means defines an ablation target of the scar tissue covering the implanted lead. The sharp-edge distal end of the electrode means is positioned to directly face the target scar tissue. A RF current is applied to the electrode means and the tissue temperature rises from the baseline body temperature to about a transitional temperature for Nitinol sheet member, for example 50-degree Celsius. When the plurality sheet members of the electrode means encounter said transitional temperature, the memory-shaped Nitinol sheet members turn inwardly and apply a pressure to the contact tissues. Each of the Nitinol sheet members is pre-shaped so that a circular enclosure formed by the distal ends of all the sheet members is about the diameter of the lead to be extracted. The Nitinol sheet members maintain this shape as long as the temperature is at or above the transitional temperature. After separating the scar tissue from the lead, the RF current is turned off and the temperature of the surrounding tissues drops to below the transitional temperature. The Nitinol sheet members return to its original shape at a temperature below the transitional temperature.

A conducting wire, which is attached to the electrode means, passes through the electrode lumen of the guiding shaft and through the interior cavity of the handle, and is thereafter secured to a contact pin of the connector at the proximal end of the handle. Therefrom, the conducting wire is connected to an external RF generator for RF current delivery.

During lead extraction operations, the lead extraction system comprised of an outer guiding shaft and a retractable inner catheter is inserted into the body through a natural body opening by sliding over an existing lead. After the system approaches the target scar tissue mass to be treated, the tip section of the retractable inner catheter is deployed by the deployment controller mounted on the handle. Once positioned, the sharp-edge distal ends of the electrode means encircle the tissue mass. Applying a RF current to the electrode means heats the contact tissue. When the sheet members of the electrode means encounter a preset transitional temperature, for example 50° C., the Nitinol sheet members changes the shape to point the distal end inwardly. By a simultaneous or alternate mode, gradually pushing forward the inner catheter against the tissue mass and applying RF current, the target tissue mass is loosened as a result of a combination of the RF energy and mechanical cutting of the sharp ends of the electrode means.

A fluid source is positioned at the proximal end of the handle for supplying a fluid flow through one of the lumens of the guiding shaft to the tip section, which contains a fluid vent opening. Therefore, at or after the ablation time, the fluid is continuously or intermittently supplied through the opening to cover and rinse the tissue contact site of the electrodes so that the impedance rise at the contact site is substantially reduced. The appropriate fluid flow rate for fluid irrigation is preferably in the range of 5 cc/min to 20 cc/min. By cooling off the electrode during RF current delivery, results in optimal ablation efficiency, and an efficient cutting loosens the scar tissues surrounding the implanted lead. Therapeutic fluid can also be supplied.

A fluid conveying lumen is associated with the guiding shaft or an inner catheter, and is preferably disposed of within a separate lumen of the guiding shaft along the longitudinal axis thereof. The lumen is adapted to communicate with the fluid supplying source, to convey fluid from the source and through the lumen to be discharged through the vent opening of the tip section and diffused out of the tip section of the lead extraction system.

This invention also comprises a method and a system for controlling the flow rate of fluid through the lumen to optimize the cooling effect of the energy delivering electrode means of the lead extraction system. The control system preferably regulates the flow rate based on signals representative of the temperature of the electrode tip and/or tissue impedance.

In an additional embodiment, the lead extraction system further comprises a temperature sensing and a closed-loop temperature controller for the electrode means having a temperature sensor close to the tissue contact site. Temperature sensing wires along with a thermocouple or thermister means is provided to transmit the temperature data from the tissue contact site to an external temperature measuring and controller. An algorithm is equipped for the ablation system so that the closed-loop temperature control is effective and the temperature data is relayed to an external RF generator for controlling RF current delivery.

In a further embodiment, the material of the electrode is selected from the memory-shaped Nitinol or other appropriate material. In particular, a sharp-edge electrode means composed of Nitinol with its shape-memory property can change its shape or position to more effectively loosen the surrounding tissue from the implanted lead. After the lead and its surrounding tissue is loosened, a locking stylet is optionally used to engage the lead with the lead extraction system and the lead is removed by said lead extraction system thereafter.

The system and methods of the present invention have several significant advantages over the currently known lead extraction systems or methods. In particular, the electrode means comprising a memory-shaped Nitinol and having RF ablation capabilities of this invention result in a more effective means for cutting loose the scar tissue and has a more effective means for removing the undesired lead from the implanted site.

BRIEF DESCRIPTION OF THE DRAWINGS

Additional objectives and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
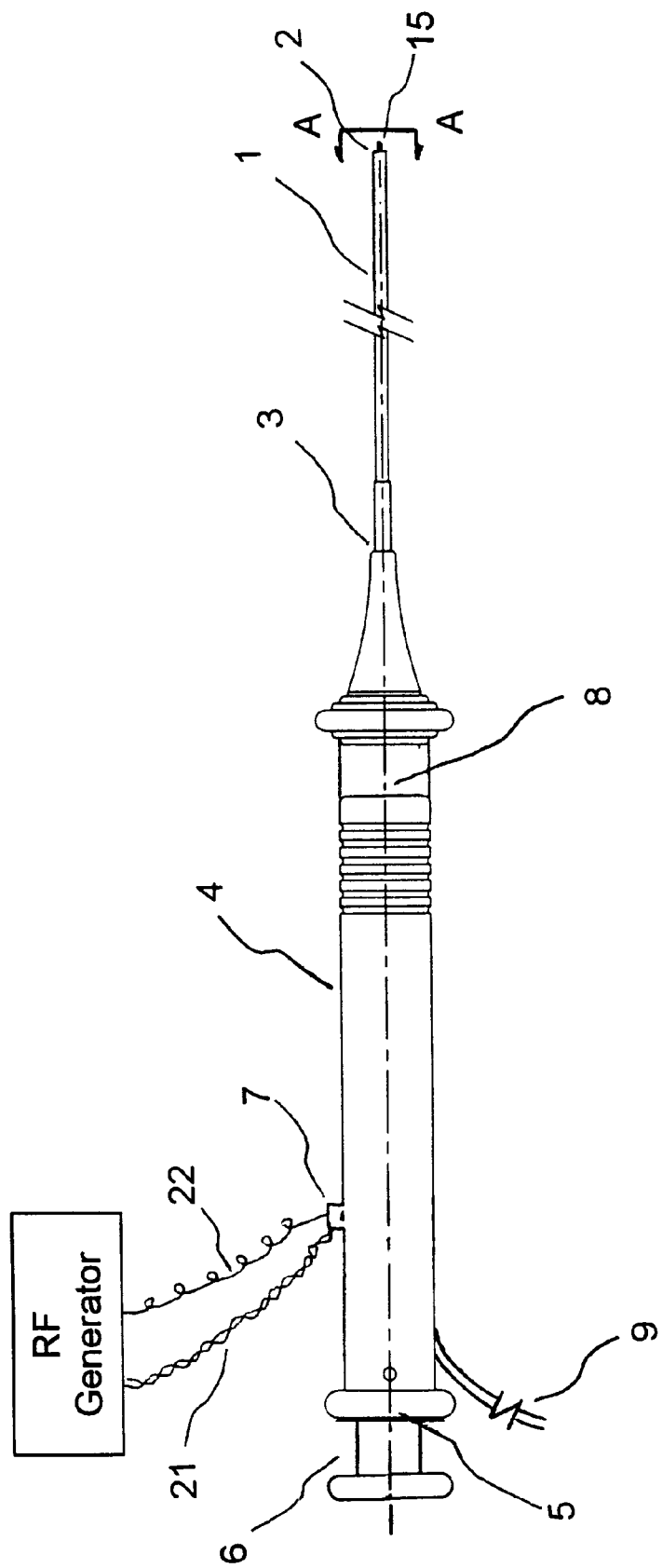
FIG. 1 is an overall view of the lead extraction system containing an electrode means having a plurality of memory-shaped Nitinol sheet members at its distal tip section constructed in accordance with the principles of the present invention.

A lead extraction system constructed in accordance with the principles of the present invention is comprised of an outer guiding shaft and a retractable inner catheter. FIG. 1 shows an overall view of the lead extraction system comprising a guiding shaft 1 having a shaft distal end 2, a shaft proximal end 3, and at least one lumen 18, 19 extending between the shaft distal end 2 and the shaft proximal end 3. A handle 4 is attached to the shaft proximal end 3 of the guiding shaft 1, wherein the handle 4 has a cavity 8. A retractable inner catheter 11 is located inside the at least one lumen 18 of the guiding shaft 1, wherein the retractable inner catheter 11 has a distal end 12 and a proximal end 5. An electrode means 15 having a plurality of sheet members 13 is secured to the distal end 12 of the retractable inner catheter 11. Each of the plurality sheet members 13 of the electrode means 15 has a proximal end and a sharp-edge distal end 14, wherein the proximal ends of the plurality sheet members 13 are joined at the distal end 12 of the retractable inner catheter 11. An electrical conductor 22 is attached to the electrode means 15. A deployment controller 6 is mounted on the handle 4 and is secured to the proximal end 5 of the retractable inner catheter 11. The deployment controller 6 has a deployed state for the retractable inner catheter 11 to deploy outside of the shaft distal end 2 of the guiding shaft 1 and the deployment controller 6 also has a non-deployed state for the retractable inner catheter 11 to be retracted within the at least one lumen of the guiding shaft 1.

A connector means 7 for the conducting wire 22 to be used to transmit the RF current and for the temperature sensing wires 21 is located on the handle 4 of the lead extraction system. A fluid irrigation means 9 is located close to the proximal end of the handle 4.

Figure 2:
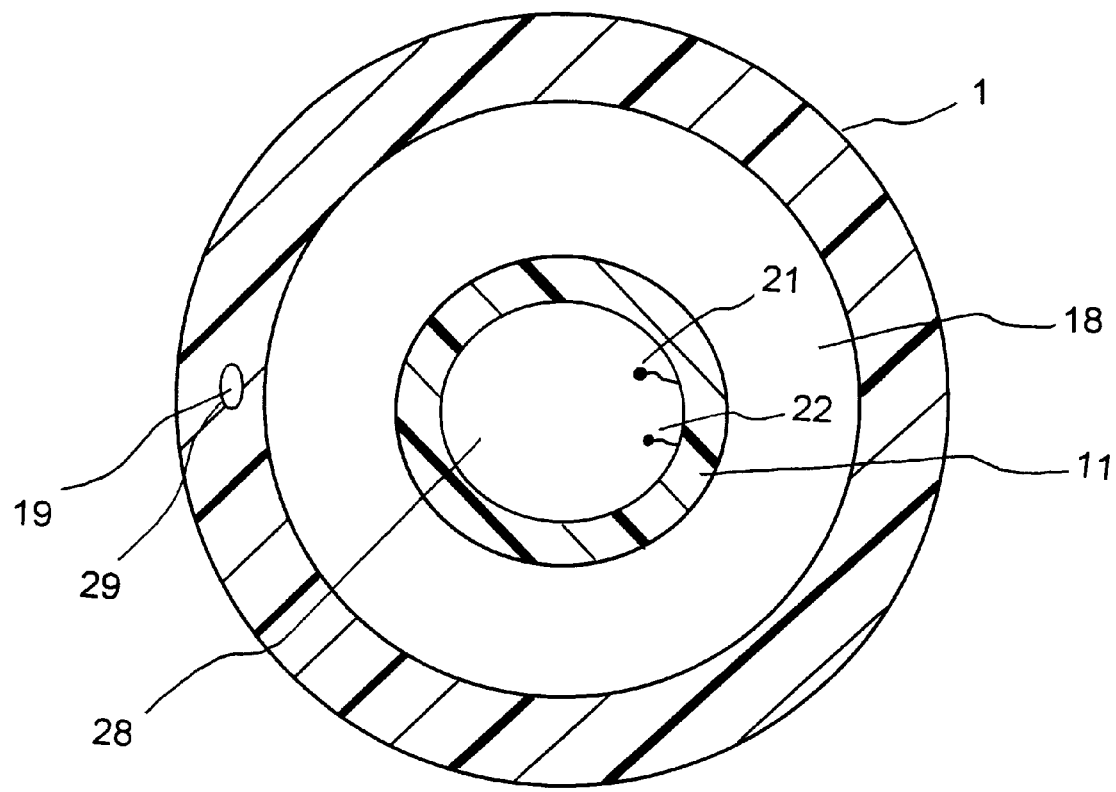
FIG. 2 is a transverse view of the A—A section of FIG. 1 showing the plurality of lumens of the guiding shaft.

FIG. 2 shows a transverse view of the A—A section of FIG. 1, whereby it shows the at least one lumens 18, 19 of the guiding shaft 1. In one embodiment, the lumen 19 is used for conveying fluid from the fluid irrigation means 9 to the fluid venting opening 29. The fluid is selected from the group consisting of saline, heparin, antibiotics, anti-inflammatory agent, chemotherapy fluid, therapeutics fluid and the like. An inner catheter 11 having at least one lumen 28 is located within the at least one lumen 18 of the guiding shaft 1. The electrical conductor 22 is connected to the electrode means 15 while the temperature sensing wires 21 are connected to the temperature sensor means 20 on the electrode means 15.

Figure 3A:
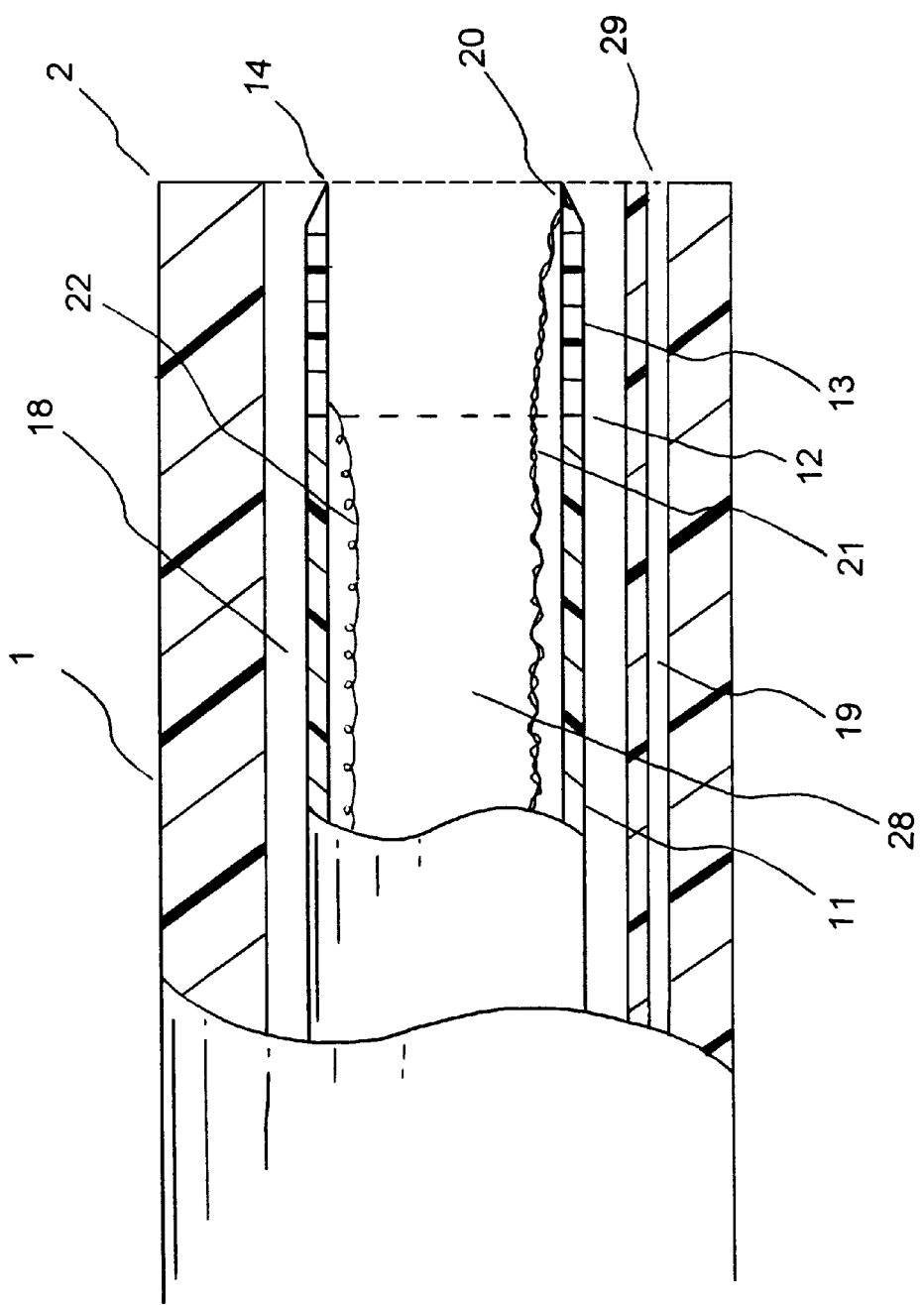
FIG. 3A is a side view of the distal section of the guiding shaft of the lead extraction system of the present invention at a non-deployed state.
Figure 3B:
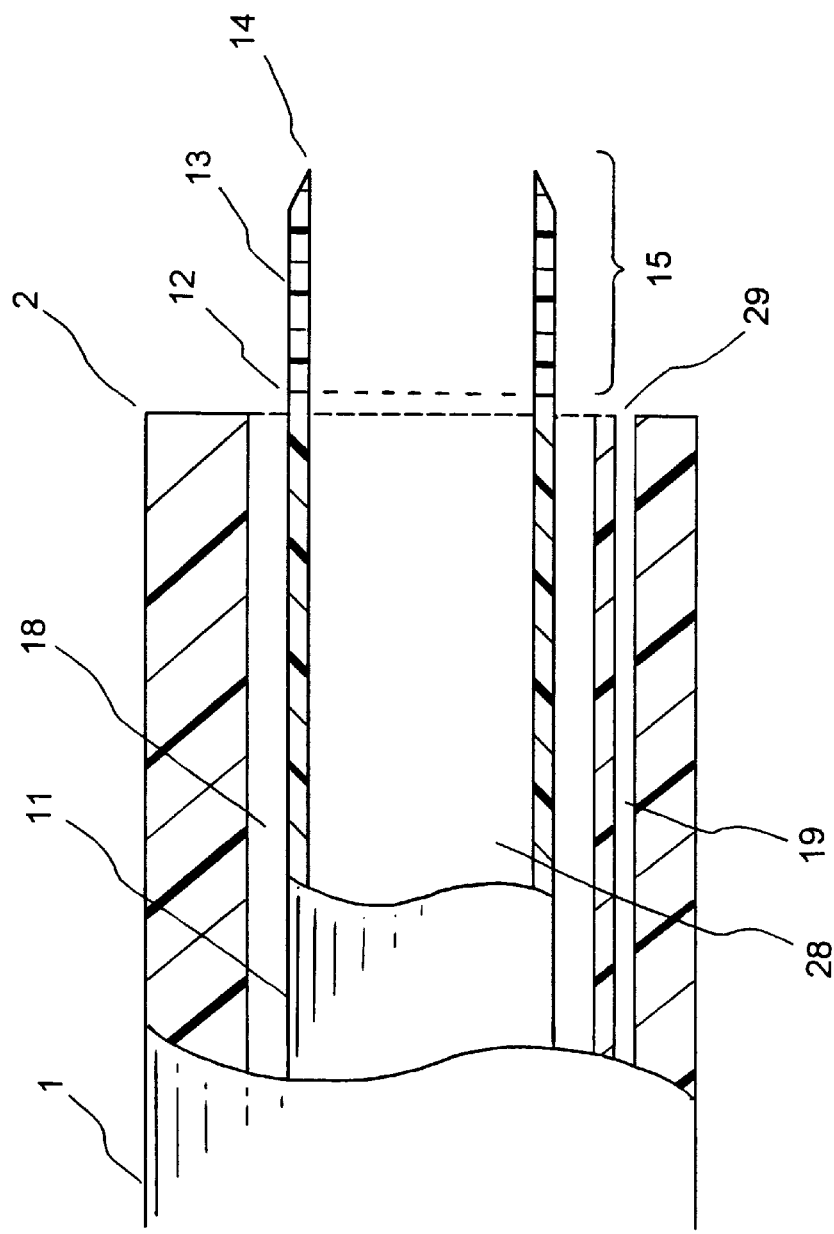
FIG. 3B is a side view of the distal section of the guiding shaft of the lead extraction system of the present invention at a deployed state.

FIG. 3A shows a side view of the distal section of the guiding shaft 1 of the lead extraction system of the present invention at a non-deployed state. Under a non-deployed state, the retractable inner catheter 11 along with the distal end 14 of the electrode means 15 stays within the lumen 18 of the guiding shaft 1. And the plurality of sheet members 13 of the electrode means 15 has its original shape that is parallel to the axis of the guiding shaft 1. Under a deployed state as shown in FIG. 3B, the retractable inner catheter 11 is deployed so that the electrode portion 15 is out of the distal end 2 of the guiding shaft 1. At this time, the sheet members 13 of the electrode means 15 have their original shape, which is parallel to the axis of the guiding shaft 1.

Figure 3C:
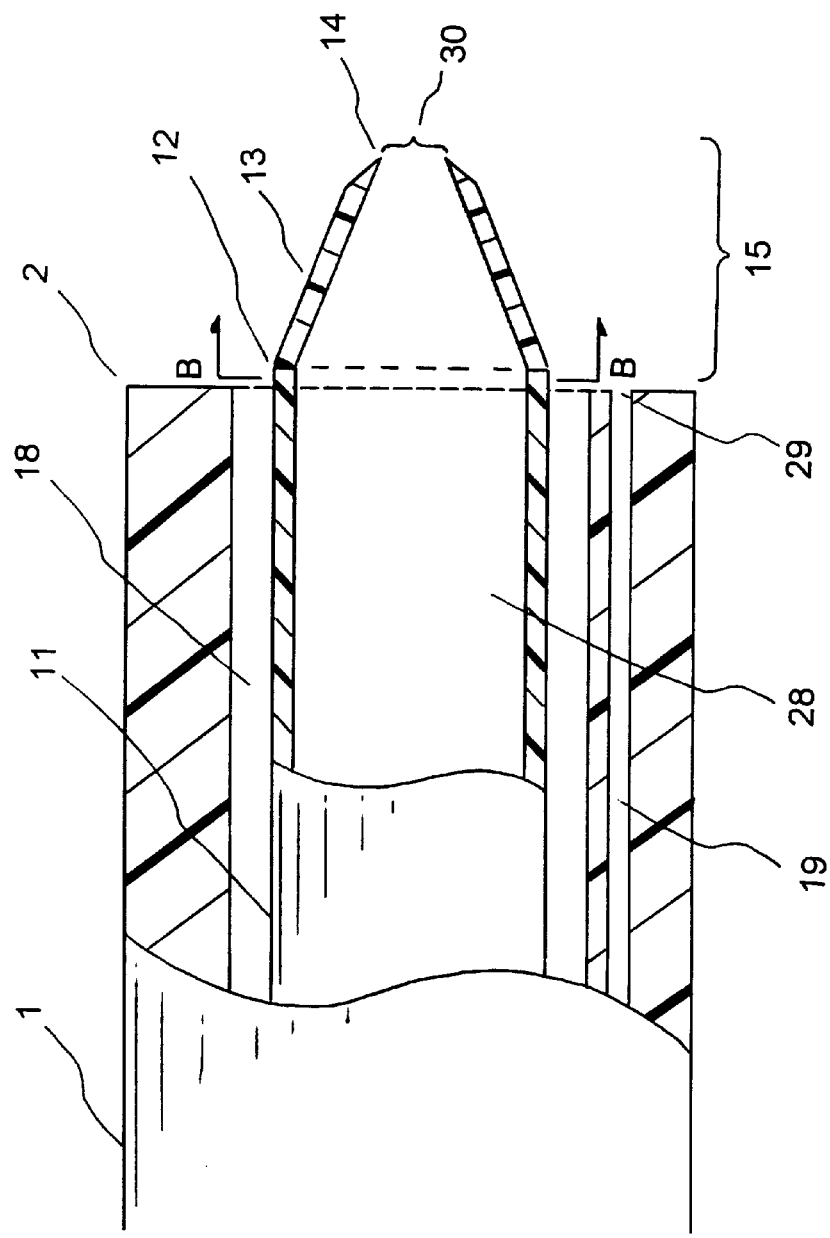
FIG. 3C is a side view of the distal section of the guiding shaft of the lead extraction system of the present invention at a deployed state when the Nitinol sheet members are activated.

FIG. 3C shows a side view of the distal section of the guiding shaft 1 of the lead extraction system of the present invention at a deployed state when the memory-shaped Nitinol sheet members 13 are activated. The deployed electrode means defines an ablation target of the scar tissue covering the implanted lead. The sharp-edge distal end 14 of the electrode means is positioned to directly face the target scar tissue. A RF current is applied to the electrode means 15 and the tissue temperature rises from the baseline body temperature of about 37° C. to about a transitional shape-change temperature for Nitinol sheet member, for example 50° C. When the sheet members 13 of the electrode means 15 encounter said transitional temperature, the memory-shaped Nitinol sheet members 13 turn inwardly. Each of the Nitinol sheet members 13 is pre-shaped inwardly so that a circular enclosure 30 is formed by the distal ends 14 of all the sheet members. The diameter of the circular enclosure 30 is about the diameter of the lead to be extracted. The Nitinol sheet members 13 maintain this shape as long as the temperature is at or above the transitional temperature. After separating the scar tissue from the lead, the RF current is turned off and the temperature of the surrounding tissues drops to below the transitional temperature. The Nitinol sheet members 13 then return to their original shape at a temperature below the transitional temperature. The RF current is preferably within the range of 50 to 2,000 kHz.

Figure 4:
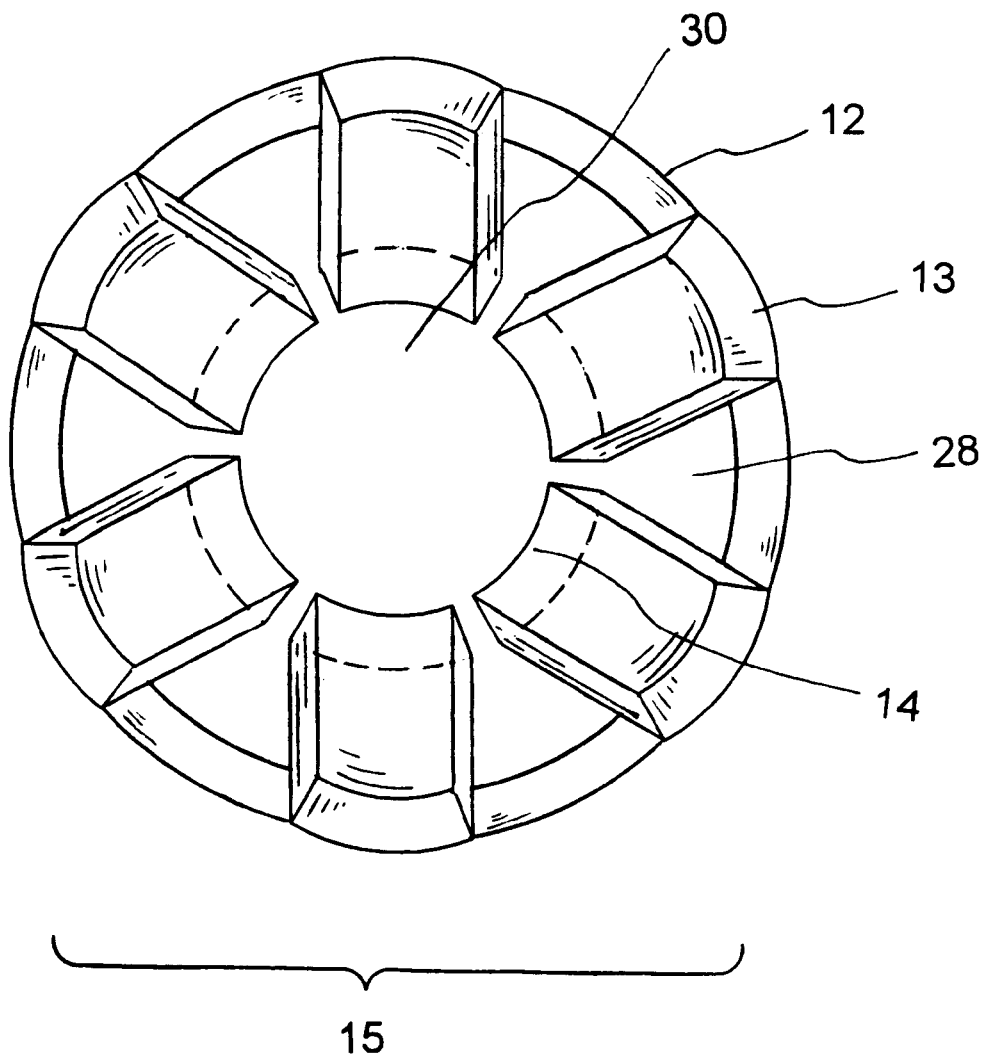
FIG. 4 is a transverse view of the distal end of the inner catheter of the B—B section of FIG. 3C.

FIG. 4 shows a transverse view of the distal end 12 of the inner catheter of the B—B section of FIG. 3C. The enclosure 30 is about the same diameter of the lead to be extracted. Therefore, when RF current is applied, the sharp-edge distal ends 14 of the electrode means 15 cut into the attached scar tissue to loosen and separate it from the lead.

Figure 5:
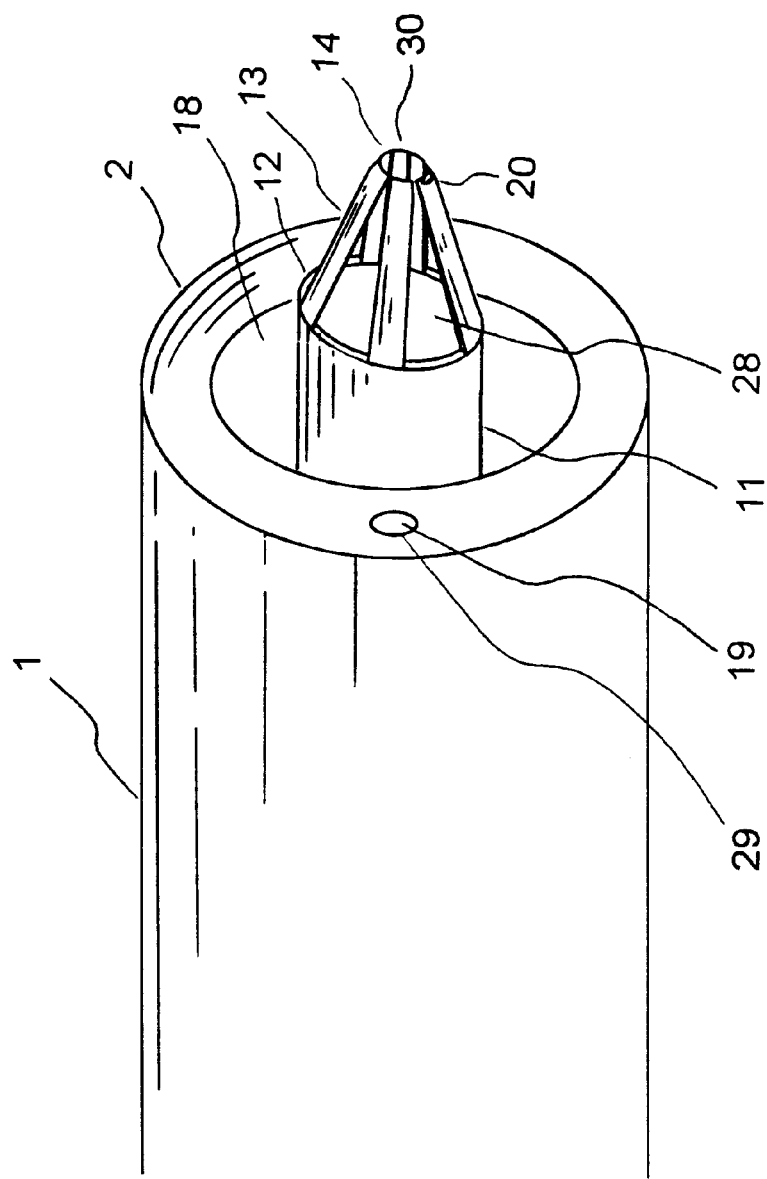
FIG. 5 is a perspective view of the distal tip section of the lead extraction system of the present invention.

FIG. 5 shows a perspective view of the distal tip section of the lead extraction system of the present invention. The Nitinol sheet members 13 of the electrode portion are conductive and can deliver RF energy when it contacts the tissue. The sharp edge 14 of the electrode 15 is used to cut through the scar tissue associated with the implanted lead. The cutting operation is achieved by a combination of advancing the electrode means, and/or heating the electrode means. The surfaces of the guiding shaft and the inner catheter are not conductive.

In a farther embodiment, the lead extraction system may further comprise a stylet locking mechanism at the handle for controlling the advancement and locking activities of the locking stylet of the guiding shaft. A stylet-locking plunger of the locking mechanism at the handle is used to control the degree of the advancement of the locking stylet of the guiding shaft. The stylet locking mechanism on the lead extraction system is well known to those who are skilled in the art.

In an additional embodiment, the lead extraction system further comprises a temperature sensing and closed-loop temperature controller for the electrode means 15 having a temperature sensor 20 close to the tissue contact site. Temperature sensing wires 21 along with a thermocouple or thermister means is provided to transmit the temperature data from the tissue contact site to an external temperature measuring and control apparatus. An algorithm is equipped for the ablation system so that a closed-loop temperature control is effective and the temperature data is relayed to an external RF generator for controlled energy delivery.

From the foregoing, it should now be apparent that an improved lead extraction system comprised of an electrode means having shape-memory capability with a RF energy delivery capability has been disclosed for removing the implanted lead from a patient. While this invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A lead extraction system comprising:
   a guiding shaft having a shaft distal end, a shaft proximal end, and at least one lumen extending between the shaft distal end and the shaft proximal end;
   a handle attached to the shaft proximal end of the guiding shaft, wherein the handle has a cavity;
   a retractable inner catheter located inside the at least one lumen of the guiding shaft, wherein the retractable inner catheter has a distal end and a proximal end;
   an electrode means having a plurality of sheet members secured to the distal end of the retractable inner catheter, each of the plurality sheet members of the electrode means having a proximal end and a sharp-edge distal end, wherein the proximal ends of the plurality of sheet members are joined at the distal end of the retractable inner catheter, and wherein an electrical conductor is attached to the electrode means; and
   a deployment controller mounted on the handle and secured to the proximal end of the retractable inner catheter, the deployment controller having a deployed state for the retractable inner catheter to deploy outside of the shaft distal end of the guiding shaft, and the deployment controller having a non-deployed state for the retractable inner catheter to be retracted within the at least one lumen of the guiding shaft.

2. The lead extraction system of claim 1 further comprising a RF current generator, wherein the RF current is delivered to the electrode means.

3. The lead extraction system as in claim 1, wherein the sheet members of the electrode means are made of a memory-shaped Nitinol, and wherein the Nitinol has a transitional shape-change temperature.

4. The lead extraction system of claim 1 further comprising a means for supplying fluid to the shaft distal end of the guiding shaft and diffused out of the shaft distal end of the guiding shaft.

5. The lead extraction system as in claim 4, wherein the fluid is selected from the group consisting of saline, heparin, antibiotics, anti-inflammatory agent, chemotherapy fluid, and therapeutics fluid.

6. The lead extraction system as in claim 3, wherein the transitional shape-change temperature for the memory-shaped Nitinol is about 50 degree Celsius.

7. The lead extraction system as in claim 6, wherein the memory-shaped Nitinol is activated by the RF current from a RF current generator.

8. The lead extraction system of claim 2 further comprising at least one temperature sensing means and a closed-loop temperature controller for the lead extraction system, wherein a temperature sensed by the temperature sensing means is relayed to the closed-loop temperature controller to effect the control of the RF current to the electrode means.

9. The lead extraction system of claim 4 further comprising a system for controlling the flow rate of the fluid through the electrode lumen of the guiding shaft.

10. The lead extraction system as in claim 2, wherein the RF current is within the range of 50 to 2,000 kHz.

11. A method for operating a lead extraction system to separate a scar tissue from the lead, the lead extraction system comprising a guiding shaft and a retractable inner catheter, wherein the retractable inner catheter has a distal end and a proximal end; an electrode means having a plurality of sheet members secured to the distal end of the retractable inner catheter, each of the plurality sheet members of the electrode means having a proximal end and a sharp-edge distal end, wherein the proximal ends of the plurality sheet members are joined at the distal end of the retractable inner catheter, and wherein an electrical conductor is attached to the electrode means; and a deployment controller mounted on the handle and secured to the proximal end of the retractable inner catheter, the deployment controller having a deployed state for the retractable inner catheter to deploy outside of the shaft distal end of the guiding shaft, the deployment controller having a non-deployed state for the retractable inner catheter to be retracted within one of the plurality of lumens of the guiding shaft; and a RF current generator, wherein the RF current is delivered to the electrode means; the method comprising steps of:
(a) sliding the lead extraction system over an existing lead in a patient;
(b) intimately contacting the distal end of the catheter sheath with a scar tissue on the lead;
(c) deploying the retractable inner catheter;
(d) applying RF current to the electrode means;
(e) extracting the lead by pulling the system out of a patient.

12. The method for operating the lead extraction system as in claim 11 further comprising supplying a fluid to the guiding shaft.

13. The method for operating the lead extraction system of claim 11, wherein the sheet members of the electrode means are made of a memory-shaped Nitinol, and wherein the Nitinol has a transitional shape-change temperature.

14. The method for operating the lead extraction system of claim 12, wherein the fluid is selected from the group consisting of saline, heparin, antibiotics, anti-inflammatory agent, chemotherapy fluid, and therapeutics fluid.

15. The method for operating the lead extraction system as in claim 11 further comprising at least one temperature sensing means and a closed-loop temperature controller for the lead extraction system, wherein a temperature sensed by the temperature sensing means is relayed to the closed-loop temperature controller to effect the control of the RF current to the electrode means.

16. A method for operating a lead extraction system to separate a scar tissue from the lead, the lead extraction system comprising: a guiding shaft having a shaft distal end, a shaft proximal end, and a plurality of lumens extending between the shaft distal end and the shaft proximal end; a handle attached to the shaft proximal end of the guiding shaft, wherein the handle has a cavity; a retractable inner catheter located inside one of the plurality of lumens of the guiding shaft, wherein the retractable inner catheter has a distal end and a proximal end; an electrode means having a plurality of sheet members secured to the distal end of the retractable inner catheter, each of the plurality sheet members of the electrode means having a proximal end and a sharp-edge distal end, wherein the proximal ends of the plurality sheet members are joined at the distal end of the retractable inner catheter, and wherein an electrical conductor is attached to the electrode means; a deployment controller mounted on the handle and secured to the proximal end of the retractable inner catheter, the deployment controller having a deployed state for the retractable inner catheter to deploy outside of the shaft distal end of the guiding shaft, and the deployment controller having a non-deployed state for the retractable inner catheter to be retracted within one of the plurality of lumens of the guiding shaft; and a RF current generator, wherein the RF current is delivered to the electrode means;

the method comprising steps of:
(a) sliding the lead extraction system over an existing lead in a patient;
(b) intimately contacting the distal end of the catheter sheath with a scar tissue on the lead;
(c) deploying the retractable inner catheter;
(d) applying RF current to the electrode means;
(e) extracting the lead by pulling the system out of a patient.

17. The method for operating the lead extraction system as in claim 16, further comprising supplying a fluid to the guiding shaft.

18. The method for operating the lead extraction system of claim 17, wherein the fluid is selected from the group consisting of saline, heparin, antibiotics, anti-inflammatory agent, chemotherapy fluid, and therapeutics fluid.

19. The method for operating the lead extraction system of claim 16, wherein the sheet members of the electrode means are made of a memory-shaped Nitinol, and wherein the Nitinol has a transitional shape-change temperature.

20. The method for operating the lead extraction system as in claim 16 further comprising at least one temperature sensing means and a closed-loop temperature controller for the lead extraction system, wherein a temperature sensed by the temperature sensing means is relayed to the closed-loop temperature controller to effect the control of the RF current to the electrode means.

* * * * *